United States Patent [19]

Meyer et al.

[11] Patent Number: 5,241,088

[45] Date of Patent: Aug. 31, 1993

[54] NON-CATALYTIC OXIDATION OF ALKYLENE TO ALKYLENE OXIDE IN THE PRESENCE OF RECYCLED ALDEHYDE BY-PRODUCTS

[75] Inventors: James L. Meyer, Lake Charles; Buford T. Pennington, Sulphur; Michael C. Fullington, Lake Charles, all of La.

[73] Assignee: Olin Corporation, Cheshire, Conn.

[21] Appl. No.: 876,600

[22] Filed: Apr. 30, 1992

Related U.S. Application Data

[63] Continuation-in-part of Ser. No. 741,377, Aug. 7, 1991, Pat. No. 5,117,011.

[51] Int. Cl.$^5$ .................. C07D 301/08; C07D 303/04
[52] U.S. Cl. .................................................. 549/523
[58] Field of Search ............................................. 549/523

[56] References Cited

U.S. PATENT DOCUMENTS

| | | | |
|---|---|---|---|
| 1,995,991 | 3/1935 | Lenher | 260/156.5 |
| 2,392,316 | 1/1946 | Dreyfus | 260/533 |
| 2,530,509 | 11/1950 | Cook | 260/348.5 |
| 2,689,253 | 9/1954 | Robertson et al. | 260/451 |
| 3,026,333 | 3/1962 | Wegner et al. | 260/348.5 |
| 3,132,156 | 5/1964 | Lemon et al. | 260/348 |
| 3,324,093 | 6/1967 | Alleman | 260/88.2 |
| 3,483,229 | 12/1969 | Bernard | 260/348.5 |
| 4,242,531 | 12/1980 | Carter | 585/512 |
| 4,785,123 | 11/1988 | Pennington | 549/532 |
| 4,943,643 | 7/1990 | Pennington et al. | 549/552 |
| 4,992,567 | 1/1991 | Meyer et al. | 549/532 |
| 5,117,011 | 5/1992 | Pennington et al. | 549/523 |

FOREIGN PATENT DOCUMENTS

986127 3/1976 Canada ................................ 549/523
960332 6/1964 United Kingdom .

OTHER PUBLICATIONS

Geddes, K. R. "The Loop Reactor Process" appearing in Proceedings of the International Conference on Organic Coatings Science and Technology, 11th International Conference) at pp. 47–62 (1985).

Primary Examiner—Joseph E. Evans
Attorney, Agent, or Firm—Dale Lynn Carlson

[57] ABSTRACT

A non-catalytic, gas-phase oxidation process for the production of an alkylene oxide or mixture of alkylene oxides in the presence of an aldehyde which may be an aldehyde produced in the oxidation process. Preferably, a gaseous mixture of propylene, oxygen and acetaldehyde is reacted at a temperature in the range of from about 200 to about 350° C. and at a superatmospheric pressure up to about 1000 psig.

13 Claims, 1 Drawing Sheet

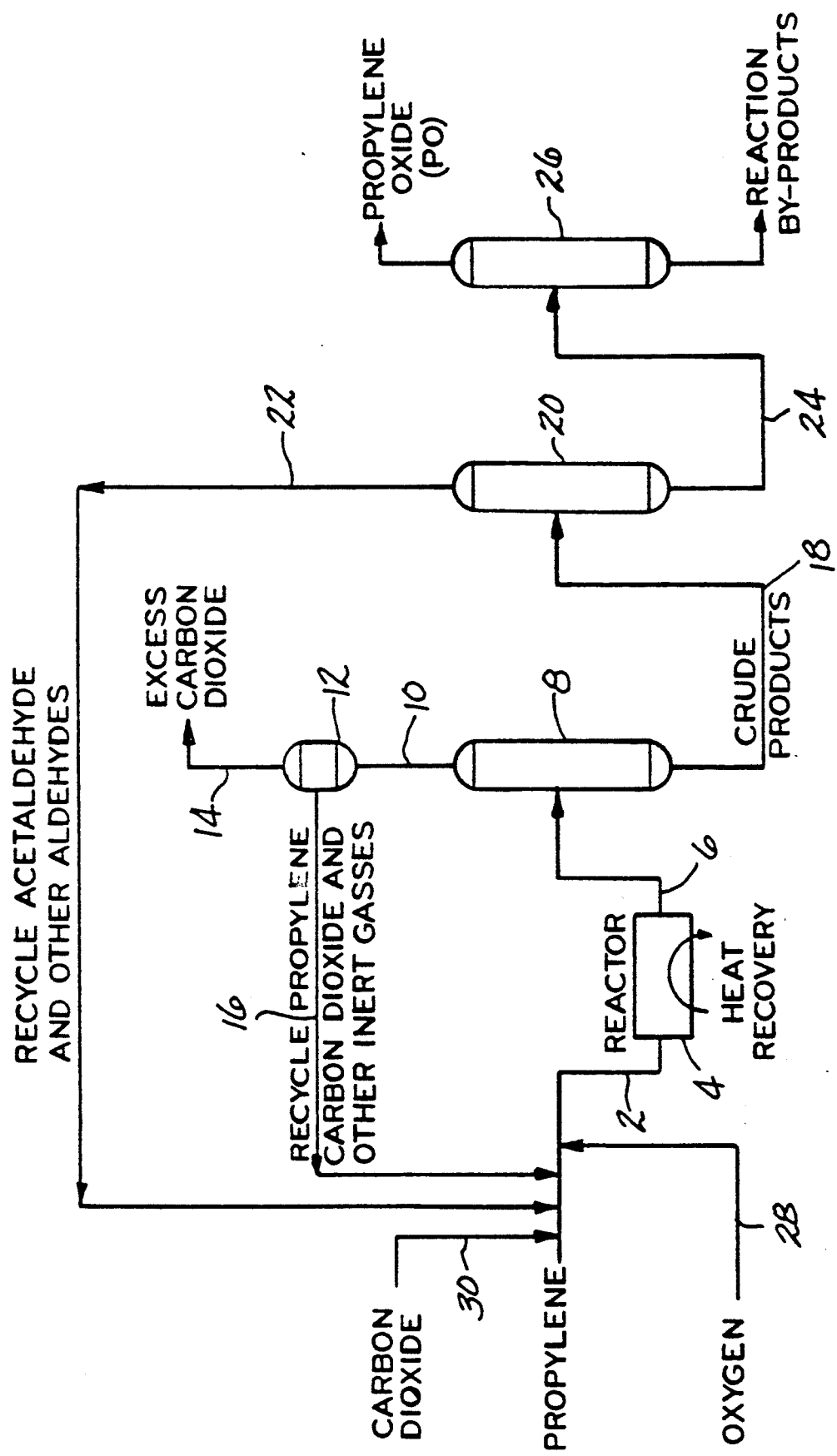

NON-CATALYTIC OXIDATION OF ALKYLENE TO ALKYLENE OXIDE IN THE PRESENCE OF RECYCLED ALDEHYDE BY-PRODUCTS

CROSS-REFERENCE TO RELATED APPLICATION

This is a continuation-in-part of U.S. patent application Ser. No. 07/741,377, filed Aug. 7, 1991, now U.S. Pat. No. 5,117,011, the entire disclosure of which is incorporated herein by reference.

FIELD OF THE INVENTION

This invention relates to a process for the direct oxidation of alkylenes and alkanes. In particular, propylene oxide is produced in an isothermal reaction, which does not require the presence of a catalyst, using recirculation of aldehyde by-products to enhance reaction stability and increase overall yield of propylene oxide.

BACKGROUND OF THE INVENTION

Alkylene oxides (vicinal epoxy alkanes), and particularly propylene oxide, are widely used chemicals. The alkylene oxides have been polymerized with a wide variety of monomers to yield polymers which are useful in coating compositions and in the manufacture of molded articles such as urethane foams. They are also reacted with alcohols to yield monoalkyl ethers which have utility as solvents in many commercial processes and which are useful as components for synthetic turbo-jet lubricants.

Many methods to produce propylene oxide are known throughout the art. One method, referred to as the chlorohydrin process, involves the reaction of chlorine and water to form hypochlorous acid which is then reacted with propylene forming propylene chlorohydrin. The propylene chlorohydrin is then dechlorinated to yield propylene oxide.

U.S. Pat. Nos. 4,785,123 and 4,943,643 to Pennington, disclose vapor phase oxidation of olefins by bubbling the gases through a molten nitrate salt catalyst. The salts are a mixture of potassium and sodium salts containing 20-80 wt. % sodium nitrate. The presence of these salts serves as an isothermal medium which absorbs large quantities of heat generated during the exothermic oxidation reaction.

Non-catalytic oxidation reactions have also been disclosed. Co-pending U.S. patent application 07/620,675 by Fullington, filed Dec. 3, 1990, discloses the direct oxidation of propylene with oxygen. The operating temperature is from 100° C. to 300° C. at a pressure above 300 psia (pounds per square inch absolute).

U.S. Pat. No. 2,530,509 by Cook discloses reacting propane and propylene with oxygen in a plug flow reactor having a large surface area relative to the volume occupied by the reacting gases. The large surface area is required to remove heat generated during the oxidation reaction. While the direction of gas flow may be reversed, there is no suggestion of circulating the gases to obtain an isothermal reaction zone.

U.S. Pat. No. 3,132,156 to Lemon et al. discloses a reaction vessel for the oxidation of propylene which provides substantial homogeneity of reactants and essentially isothermal conditions throughout the reaction zone. The reaction temperature is maintained within the range of 425° C. to 575° C.

U.S. Pat. No. 4,992,567 to Meyer et al discloses the vapor phase oxidation of an alkane or olefin in molten salt catalyst in the presence of an aldehyde normally formed in the oxidation process, which aldehyde is separated from the reaction product and recirculated back into the oxidation phase reaction for co-oxidation to form carbon-oxygen gases while increasing the olefin selectivity to alkylene oxide. Reaction temperatures are in the range of about 135°-600° C. and the reaction pressures are in the range of about 1-50 atmospheres.

Non-catalytic direct oxidation has advantages over catalyzed oxidation or processes requiring intermediate reaction steps. There are fewer process steps to monitor and fewer chemical components to maintain, both of which reduce cost. However, until now, non-catalytic direct oxidation has been limited by low yield and poor propylene oxide selectivity. Propylene oxide selectivity is the molar percentage of propylene oxide produced for every mole of propylene which reacts within the reactor vessel.

SUMMARY OF THE INVENTION

Accordingly, it is an object of the present invention to provide a process for the non-catalytic oxidation of alkylenes, such as propylene, which has a higher yield than prior art processes. It is a feature of the invention that by recycling at least a portion of aldehyde by-products to the reactor and maintaining the reaction temperature, pressure and time within critical operating parameters, both high alkylene oxide yields and selectivity are obtained. Yet another feature of the invention is that the flow of gases within the reaction vessel provide an essentially isothermal reaction.

One advantage of the invention is that the reaction does not require the presence of a catalyst. In the case of the production of propylene oxide by this process, the molar percent of reacted propylene converted to propylene oxide has been measured to be in excess of 40%. Yields in excess of 50% are believed obtainable with the process.

Accordingly, there is provided an oxidation process for the production of an alkylene oxide or mixture of alkylene oxides in the presence of an aldehyde or mixtures of aldehydes which may be produced in the oxidation process. A gaseous mixture containing at least one hydrocarbon selected form the group consisting of alkylenes, alkanes and derivatives thereof, oxygen and the aldehyde are circulated in a reaction vessel. The hydrocarbon is oxidized under essentially non-catalytic, substantially isothermal conditions while the partial pressure of the hydrocarbon is maintained at from about 80 to about 600 psia and the reaction temperature is maintained at from about 200° C. to about 350° C.

The above stated objects, features and advantages as well as others will become more apparent from the specification and drawing which follow.

IN THE DRAWING

The drawing shows a schematic flow diagram illustrating a continuous process for carrying out the production of propylene oxide in accordance with the invention.

DESCRIPTION OF THE INVENTION

The present invention is based upon the discovery that the yield of alkylene oxide produced by a non-catalytic oxidation process can be substantially increased by a continuous by-product recycle process in which the advantages of the non-catalytic oxidation process are enhanced by isolating and recycling the aldehyde by-products, whereby the overall selectivity of olefin to alkylene oxide is substantially increased approaching 60%, undesirable low value aldehydes are consumed.

The hydrocarbons useful as reaction gases to be oxidized by the process of the invention can be broadly defined as alkylenes and alkanes having at least 3 carbon atoms. This definition is intended to include terminal olefins selected from the group consisting of monofunctional and difunctional olefins having the following structural formulas, respectively:

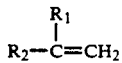 (I)

where $R_1$ is hydrogen or an alkyl chain, straight or branched, having 1 to 20 carbon atoms and $R_2$ is an alkyl chain, straight or branched, having 1 to 20 carbon atoms; and:

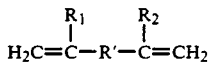 (II)

wherein $R_1$ and $R_2$ are hydrogen atoms or alkyl chains having 1 to 10 carbon atoms and R. is from 2 to 10 methylene groups. The definition also includes cyclic olefins and internal olefins. The ring portions of the cyclic olefins can have up to 10 carbon atoms and one unsaturated bond and can be substituted with one or two alkyl radicals having 1 to 10 carbon atoms. The cyclic olefins are typically represented by the following structural formula:

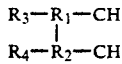 (III)

wherein $R_1$ and $R_2$ are alkylene radicals having 1 to 4 carbon atoms and $R_3$ and $R_4$ represent hydrogen atoms, or one or two alkyl radicals, straight or branched chain, having 1 to 10 carbon atoms. The internal olefins are represented by the following structural formula:

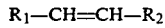 (IV)

wherein $R_1$ and $R_2$ are straight chain or branched chain alkyl radicals having 1 to 10 carbon atoms.

The alkanes, alkylenes, derivatives and mixtures thereof useful as gaseous reactants in the process of the invention generally have up to, but do not exceed, about 22 carbon atoms per molecule, preferably not more than 12 carbon atoms per molecule. When a straight chain alkylene or alkane is employed, it is preferred that such molecule not have more than five carbon atoms. When a cyclic compound is used, it is preferred that the cyclic compound not have more than 12 carbon atoms per molecule. Illustrative reactants include propane, propylene, isobutene, butane, cyclohexene and mixtures thereof. A preferred reactant within this group is propylene or a mixture of propylene and propane based on their commercial availability.

Representative other alkylene compounds or olefins are butene-1, butene-2, isobutylene, pentene-1, hexene-1, pentene-2, cyclopentene, and cyclooctene. Other representative olefins are 2-methylbutene-1, 3-methylbutene-1, heptene-1, octane, hexene-2, hexene-3, heptene-3, pentadecene-1, octadecene-1, dodecene-2, 2-methyl pentene-2, tetramethylethylene, methylethylethylene, cyclobutene, cycloheptene, 2-methylheptene-1, 2,4,4,-trimethylpentene-1,2-methylbutene-2, 4-methylpentene-2, and 2-ethyl-3-methylbutene-1.

Oxygen can be provided either as the pure gas or in a mixture with other gases. One such mixture is air which is preferred based on ready availability. Pure oxygen will be preferred in a commercial setting to minimize contamination from trace constituents.

In addition to the gaseous hydrocarbon and the oxygen, a diluent is preferably present. When propylene is provided at high partial pressure and in high concentration, thermal cracking may break apart the carbon chains. The diluent reduces the concentration of propylene to eliminate or minimize thermal cracking. Among the suitable diluents are inert gases such as nitrogen, argon, methane and carbon dioxide. Diluents having high thermal capacity and thermal conductivity are preferred to assist in the circulation of heat. The most preferred diluent is carbon dioxide generated as a by-product of the oxidation reaction.

For purposes of simplicity, the description that follows and the illustrative embodiments are directed to the preparation of propylene oxide. It will become apparent, however, that other alkylene oxides having four or more carbon atoms can be prepared in substantially the same fashion.

The drawing illustrates in schematic a gas phase continuous non-catalytic direct oxidation process for preparing propylene oxide which recycles a portion of the aldehyde produced during the reaction. All equipment, especially the reactor, is formed of a material such as 304 stainless steel which is inert to the reaction gases at operating temperatures and pressures of the reaction. The interior walls are preferably oxide free.

The feed stream 2 is located within close proximity of reactor 4. Feed gas streams of propylene, propane or mixtures thereof, oxygen and carbon dioxide are mixed in the desired ratio and introduced into reactor 4. The recycled aldehyde or mixture of aldehydes as well as the recycled propylene, carbon dioxide and other inert gases are introduced at this point also. The feed gas may be preheated to a temperature of 100° C. along with the recycle aldehyde just prior to introduction into the reactor. One exemplary means of preheating the feed gas is by steam tracing. Preheating the gas accelerates initiation of the oxidation reaction. Thus, the feed stream 2 entering reactor 4 combines both the initial gas streams of mixtures of propane and Propylene, oxygen 28, diluent carbon dioxide 30, and recycled feeds 16 of propylene (or propylene/propane) and carbon dioxide. In addition, recycled acetaldehyde or mixtures of acetaldehyde and other aldehydes 22 is added to the feed stream.

The gas feed stock, exclusive of recycled aldehydes, is preferably provided in a concentration of from about 30 to about 85 volume percent (vol. %) propylene, propane or mixtures thereof, from about 1 to about 20 vol. % oxygen and the balance $CO_2$ or other diluent. If air is the oxidant source, the ratio of oxygen to nitrogen in the air is considered in determining the feed stock ratio. More preferably, the propylene, propane or mixtures thereof, concentration is from about 40 to about 75 vol. %, the oxygen from about 2 to about 17 vol. % and the balance $CO_2$. Most preferably, the concentration of oxygen is from about 5 to about 15 vol. %.

The oxygen concentration is critical to the non-catalytic oxidation. The oxygen concentration influences the rate of the exothermic reaction. When a steady state reaction is achieved, the inflow of oxygen generates heat at a rate sufficient to balance the heat lost by conduction and as heated offgas. Preferably, from about 0.5 vol. % to about 3.0 vol. % $O_2$ remains unreacted and recovered as residual oxygen.

The olefin feed gas(es) can be passed into the reactor using a separate stream (e.g. feed tube) from the stream delivering the aldehyde and oxygen containing gas to the reactor. Alternatively, the reactant gases can be fed into the reactor together in a single stream premixed in the desired relative proportions outside the reactor as is shown in the schematic diagram.

Alternatively, the separated and recycled gaseous aldehyde or aldehyde mixture can be fed directly to the reactor by its own feed tube or said feed tube can be connected to an aldehyde supply tube through which the recycled aldehyde is combined with new aldehyde to form a uniform supply which is fed directly to the reactor or to the olefin or oxygen supply tubes. New aldehyde can be used to replace any aldehyde that is lost during the recycling process.

Any conventional reactor capable of circulating reaction gases to achieve an isothermal reaction may be utilized in this oxidation Process. Suitable continuous reactors are a tubular reactor, a stirred autoclave reactor or a gas loop reactor. A gas phase loop reactor is preferred where a large surface area is needed for removal of the heat of reaction.

Heat removal from the reactor is important to enable controlling the temperature inside the reactor within the desired range. This can be accomplished by use of a heat exchange system that brings in low temperature steam and removes a higher temperature steam which has absorbed the exothermic heat generated during the reaction. Alternatively, a water jacket can be placed to surround the reactor which will remove any heat generated by the exothermic reaction.

A gas blower can be used to continuously cycle the reaction gases through the reactor with reaction product gas being removed through outlet 6 to an absorption column 8 and distillation columns 20 and 26 for separation of the various by-products and recycle of those that can be recycled.

It is to be understood that by-products of the aldehyde oxidation are also produced during the reaction. Some dehydrogenation of the feed is also effected, particularly at higher temperatures with the temperature range noted below, and therefore, the reaction conditions are generally controlled to minimize such production. For optimum yields, the temperature of the reaction gases during oxidation is in the range of from about 200° C. to about 350° C. A more preferred range is from about 205° C. to about 300° C. while most preferred is from about 210° C. to about 275° C. Temperatures lower than about 200° C. are not recommended because they result in substantial reduction in reaction rate. Temperatures above about 325° C. are also not recommended because combustion to $CO_2$ and coking occur.

The partial pressure of propylene in the reactor affects yield. With the addition of recycled acetaldehyde or mixture of acetaldehyde and other aldehydes, there is an increase in propylene oxide yield with an increase in propylene partial pressure. The partial pressure is calculated by multiplying the total pressure (absolute) and the volume percent of propylene as determined by analytical means.

The preferred propylene partial pressure is from about 80 to about 600 psia. A more preferred partial pressure is from about 100 to about 550 psia, while a most preferred range is from about 120 to about 520 psia.

The total system pressure that can be used is from superatmospheric to about 1000 psig with the preferred range from about 120 to about 850 psig and the most preferred being from about 130 to about 750 psig.

The residence time of the gases in the reactor influences propylene oxide selectivity. As the time increases, the selectivity for propylene oxide decreases. It is therefore desirable to minimize residence time. Residence times of less than about 60 seconds are preferred. More preferred is from about 1 to about 50 seconds and most preferred is from about 5 to about 40 seconds. The selectivity of propylene oxide decreases when the residence time exceeds about 100 seconds.

The separation of the resulting by-products in order to recover the desired aldehydes for recycling can be accomplished by a wide variety of well-known procedures such as: absorption in water followed by fractional distillation, absorption, and condensation.

The gaseous reaction product mixture is removed from the reactor 4 via pipe 6 and transported to an absorption column 8. Water is used in the absorption column to absorb all the water soluble reaction product materials at neutral pH and the other non-asorbable materials such as alkylenes, carbon monoxide and carbon dioxide are removed as gases from the top of the column via pipe 10 to a carbon dioxide system separator 12 which removes excess carbon dioxide from the alkylene and the other inert gases. The alkylene is recycled to the reactor as is some of the carbon dioxide. The crude products of propylene oxide and aldehydes are removed from the bottom of the column 8 via pipe 18 and transported to a distillation column 20 for removal of volatiles and other materials which have a low affinity for water. The acetaldehyde formed during the reaction is removed here and recycled to the reactor via pipe 22. The crude alkylene oxide and other less volative reaction by-products are removed from the bottom of the column 20 via pipe 24 then transported to another distillation column 26 which performs an absorptive distillation using appropriate solvents which have an affinity for the other by-product components which are left in solution. Propylene oxide is recovered from the top of column 26 and then used as such or subjected to further purification as necessary. The remaining reaction by-products which contain the heavier products are removed from the bottom of the column 26 purified for further use, recycled, burned for fuel value or disposed of.

It has been found that providing a selected level of aldehyde in the feed stream to an oxidation reactor stabilizes the control of the reaction, increases rate of oxidation of the alkane or olefin, decreases the required reaction temperature and increases the selectivity to alkylene oxide, while maintaining good conversions. Desirably, the aldehyde in the feed stream is aldehyde produced in the reaction, separated from the reaction product and recycled to the feed stream, as is described in the above U.S. Pat. No. 4,992,567.

The process is run in a continuous operation. The order of introduction of the reactants is determined by the operator based on what is most safe and practical under prevalent conditions. Generally, the desirability of avoiding flammable gas mixtures throughout the reaction and subsequent product separation systems will dictate the desired procedures.

A preferred embodiment of the invention is directed to a continuous recycling process for producing a propylene oxide from an initial feed gas mixture comprising propylene, propane or mixtures thereof, an acetaldehyde or a mixture of acetaldehyde and other aldehydes, a diluent, and oxygen, said process comprising:

(a) oxidizing said propylene, propane or mixtures thereof, under substantially isothermal and essentially non-catalytic conditions while maintaining a reaction temperature of from about 200° to about 350° C. and a hydrocarbon partial pressure of from about 80 to about 600 psia;

(b) removing resulting gaseous mixture comprising propylene oxide, acetaldehyde or mixture of acetaldehyde and other aldehydes, other by-products, and oxygen;

(c) separating said acetaldehyde or mixture of acetaldehyde and other aldehydes from said resulting gaseous mixture comprising the propylene oxide, the acetaldehyde or mixture of acetaldehyde and other aldehydes, other by-products, and oxygen;

(d) recycling the acetaldehyde or mixture of acetaldehyde and other aldehydes in gaseous form back into the reaction mixture of step (a) in a concentration sufficient to produce a continuous gaseous co-oxidation of said propylene, propane or mixture thereof, and said aldehyde(s) which promotes reaction stability and which increases the selectivity of the propylene, propane or mixtures thereof, to form propylene oxide and thus increase overall yield of propylene oxide.

There is also a co-oxidation reaction taking place in step (a) which involves the indirect oxidation of the propylene by way of oxidation of a portion of the acetaldehyde to a free radical intermediate which epoxidizes the propylene to form Propylene oxide and carbon oxides (such as carbon dioxide and carbon monoxide). Such gas phase co-oxidation processes for producing propylene oxides from acetaldehyde increase the selectivity to propylene oxide and helps to control the reaction stability.

The particular aldehydes produced in the gas phase reaction of step (a) depend upon the particular alkylene hydrocarbons used therein. In the case of propylene, being oxidized to propylene oxide, the molar selectivity to acetaldehyde is substantial, in the area of 20–25%, with a smaller selectivity to acrolein, propionaldehyde and formaldehyde, in the area of 1–5% each. The maximum benefit in increasing the molar selectivity and yields of the alkylene oxide is gained if the fresh aldehyde, added to step (a) with the recycled aldehyde, is the same as the recycled aldehyde produced in greatest quantity in the reaction step (a), i.e. acetaldehyde in cases where the alkylene hydrocarbon is propylene.

In the recycling, the most preferred selectivity is achieved when the total amount of aldehydes entering the reactor nearly equals the total amount of aldehydes leaving the reactor. Step (d) of the present process involves recycling a substantial amount of acetaldehyde and other aldehyde by-products or mixtures thereof isolated in step (c) by fractional distillation of the gaseous by-product of step (a), for reintroduction into step (a) in combination with additional propylene, propane or mixtures thereof, acetaldehyde and oxygen or an oxygen containing gas, in order to co-oxidize the acetaldehyde and other aldehydes to give greater selectivity to propylene oxide. In this manner the overall yield or selectivity to propylene oxide is substantially increased, which is the main objective of the present process, while the large amount of acetaldehyde normally left over as a by-product of the oxidation of propylene is recycled and further co-oxidized to form carbon monoxide and carbon dioxide products.

EXAMPLE 1

The feed gases consisting of 34 volume percent propylene, 5 volume percent oxygen, 1.4 volume percent acetaldehyde and the balance nitrogen were premixed and preheated to 100°–125° C. before being injected into a 1-liter autoclave reactor. The reaction chamber was fitted with an agitator suited for rapid mixing of gaseous contents. The reactor wall was tapped and fitted with a thermocouple and two thermocouples were placed high and low inside the reaction chamber. The reaction chamber was heated externally via an electrical resistance heater. With the agitator on, the temperature differences between the three described thermocouples was typically from 1°–4° C. With the agitator off, the temperature readings of the three described thermocouples varied by 15°–20° C. Thus, demonstrating that the mixing of the system approached a continuous stirred tank condition when the agitator was on. The total gas flow was 48 liters per minute at STP. The reaction was carried out at 786 psig and at a reaction temperature of 232° C. When the conditions of temperatures and pressure are accounted for, the reactor residence time was about 36 seconds.

The reaction offgas was taken through a stainless steel line that was steam traced up to and beyond the backpressure regulator. Shortly after the backpressure regulator, the reaction offgas, now at a little above atmospheric pressure, was sent to an ice water trap to condense out the readily condensible components. After the cold trap, the gas went to a dry test meter that measured the total gas flow at that point. Each run was brought up to a lined out steady state condition before switching the gas flow to go through the cold trap and each run was allowed to continue for 6–10 hours after switching the gas flow to the cold trap. At the end of a run, the trap contents were weighed and analyzed by GC. During the run, periodic gas samples were taken of the feed gas and the product gas after the cold trap and analyzed by GC. In addition, the feed gas and product gas oxygen contents were independently monitored by a paramagnetic oxygen analyzer and an on-line mass spectrometer. The total moles of products in the cold trap liquids and the other product gas were calculated. The total amount of oxygen in the products, the amount of oxygen left unreacted, and the total amount of oxygen in the feed as determined by GC methods were then compared to the oxygen content in and out as determined by the oxygen analyzer.

In general, the oxygen mass balance as determined by these two independent methods were in good agreement. The overall oxygen mass balance was found to be 94 percent for this run. The propylene conversion was found to be 5.3 percent and the oxygen conversion was found to be 68.7%. The amount of acetaldehyde exiting the reactor was found to be 1.3 volume percent versus 1.4 volume percent entering the reactor. The difference which is the net amount of acetaldehyde consumed in the reaction was added mole for mole to the amount of propylene consumed and this corrected amount of propylene consumed was used to calculate product selectivities. The propylene oxide selectivity was found to be 41.9% and the total combined selectivity to propylene oxide plus propylene oxide derivatives was 48.2%. When a similar run was made without acetaldehyde addition in the feed gases at 30 seconds residence time, the propylene oxide selectivity was found to be 31.9% and the combined selectivity of propylene oxide plus propylene oxide derivatives was 37.9%. Thus, an increase in propylene oxide selectivity was seen when acetaldehyde was added to the feedgas. In addition, the reaction temperature that was required for the reaction to occur rose from 232° C. with acetaldehyde in the feed to 256° C. without acetaldehyde in the feed.

EXAMPLE 2

Another run was made as in Example 1 except that the feed gas was 60.4 volume percent propylene, 9.0 volume percent oxygen, 3.5 volume percent acetaldehyde, and the balance of the feed gas was nitrogen. The reactor pressure was also reduced to 424 psig. The total gas flow was reduced to 29 liters per minute to maintain a 30 second residence time. The reactor was found to operate in a stable manner at 257° C. The propylene conversion was found to be 10.1% and the oxygen conversion was found to be 91.6%. The propylene oxide selectivity was found to be 43.9% and the combined selectivity of propylene oxide plus propylene oxide derivatives was found to be 51.1%. When a run was attempted without acetaldehyde in the feed gas, the reactor behaved erratically and could not be run below 267° C. The run became too unstable to obtain mass balance results.

Any aldehyde product can be recycled to the gas phase oxidation of propylene to give smoother reactor operation and greater propylene oxide selectivity. These include acetaldehyde, formaldehyde, acrolein and propanal. In a continuous commercial situation, the amount of aldehyde entering the reactor should be equal to the amount of aldehyde leaving thereafter, in order to have a sustainable recycle operation. The equilibrium amount of acetaldehyde under the conditions of Examples 2 and 3 appears to be in the range from about 1.4 to about 3.5 volume percent. The feed levels of acetaldehyde and oxygen, as well as the residual oxygen level, can be adjusted to make the two values equal or nearly equal. This is so because controlling the residual oxygen level also controls the propylene conversion and the amount of propylene oxide produced and influences the amount of aldehyde produced and consumed.

Aldehyde levels are preferably in the range of from about 0.1 to about 5 volume percent of the feed. Preferred oxygen levels are in the ran9e of from about 5 to about 15 volume percent of the feed. Preferred propylene levels are from about 25 to about 80 volume percent of the feed. The reaction temperature is preferably in the range of from about 200° to about 350° C. The preferred partial pressure of propylene is in the range of from about 80 to about 600 psia.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims All patent applications, patents and other publications cited herein are incorporated by reference in their entirety.

What is claimed is:

1. A non-catalytic process for the production of an alkylene oxide in a continuous gas phase reactor which comprises:
    (a) reacting a hydrocarbon selected from the group consisting of an alkane or an olefin having at least three carbon atoms, or mixtures thereof, with an oxygen-containing gas in a reaction mixture at a temperature of from about 200° to about 350° C. and at a superatmospheric pressure up to about 1000 psig to produce a product mixture comprised of an alkylene oxide and an aldehyde,
    (b) separating the aldehyde from the product mixture, and,
    (c) admixing at least a portion of the separated aldehyde with the reaction mixture in an amount sufficient to maintain a substantially constant concentration of aldehyde in the reaction mixture.

2. The process of claim 1 wherein the alkane or olefin is propane or propylene and the alkylene oxide is propylene oxide.

3. The process of claim 2 wherein said aldehyde is acetaldehyde.

4. The process of claim 1 wherein said temperature ranges from about 205° to about 300° C.

5. The process of claim 1 wherein said pressure ranges from about 120 to about 850 psig.

6. The process of claim 1 wherein the reactants residence time in the reactor vessel is less than about 60 seconds.

7. The process of claim 1 wherein the reaction is carried out in the presence of a diluent selected from the group consisting of nitrogen, argon, methane, carbon dioxide and mixtures thereof.

8. The process of claim 7 wherein said diluent is either nitrogen or carbon dioxide.

9. The process of claim 3 wherein a mixture of propylene and propane is used.

10. The process of claim 9 wherein said temperature ranges from about 205° to about 300° C., said pressure ranges from about 120 to about 850 psig and the reactants residence time is from about 1 to about 50 seconds.

11. The process of claim 10 wherein said temperatures ranges from about 210° to about 275° C., said pressure ranges from about 130 to about 750 psig and the reactants residence time is from about 5 to about 40 seconds.

12. A non-catalytic process for the production of propylene oxide in a continuous gas phase reactor which comprises:
    (a) reacting oxygen with a mixture of propane and propylene under substantially isothermal and essentially non-catalytic conditions while maintaining a reaction temperature of from about 200° to about 350° C. and at a superatmospheric pressure up to about 1000 psig to form a reaction product mixture comprising propylene oxide, acetaldehyde or a mixture of acetaldehyde and other aldehydes, and other reaction by-products;
    (b) removing from the reaction product mixture the propylene oxide and acetaldehyde or mixture of acetaldehyde and other aldehydes;
    (c) separating said acetaldehyde and other aldehydes from said propylene oxide; and
    (d) recycling at least a portion of the acetaldehyde and other aldehydes in gaseous form back to the oxidizing reaction step (a) in an amount sufficient to maintain a substantially constant concentration of aldehyde in the reaction mixture to promote reaction stability and to increase overall yield of propylene oxide.

13. The non-catalytic process of claim 1 in which the concentration of aldehyde is from about 0.1 to about 5 volume percent.

* * * * *